US 6,639,075 B2

(12) United States Patent
Izumi et al.

(10) Patent No.: US 6,639,075 B2
(45) Date of Patent: Oct. 28, 2003

(54) LACTAM-ALDEHYDE COMPOUND AND PROCESS OF PREPARING SAME

(75) Inventors: Hiroshi Izumi, Tsukuba (JP); Shigeru Futamura, Tsukuba (JP)

(73) Assignee: National Institute of Advanced Industrial Science and Technology (JP)

( * ) Notice: Subject to any disclaimer, the term of this patent is extended or adjusted under 35 U.S.C. 154(b) by 13 days.

(21) Appl. No.: 10/091,459

(22) Filed: Mar. 7, 2002

(65) Prior Publication Data

US 2002/0198386 A1 Dec. 26, 2002

(30) Foreign Application Priority Data

May 28, 2001 (JP) ........................................ 2001-159742

(51) Int. Cl.$^7$ .................... C07D 221/02; C07D 313/00; C07D 305/12
(52) U.S. Cl. ........................ 546/183; 549/266; 549/321; 549/322
(58) Field of Search ................................ 540/485, 529, 540/532; 549/266, 321, 322; 546/183

(56) References Cited

PUBLICATIONS

Tetrahedron Letters, vol. 36, No. 22, 1995, pp. 3817–3820.
Bulletin of the Korean Chemical Society, vol. 17, No. 12, 1996, pp. 1099–1101.
Bulletin of the Korean Chemical Society, vol. 17, No. 6, 1996, pp. 564–567.
Tetrahedron Letters, vol. 36, No. 16, 1995, pp. 2827–2830.
Journal of the Americal Chemical Society, vol. 113, 1991, pp. 201–209.

*Primary Examiner*—Samuel Barts
*Assistant Examiner*—Sikarl A. Witherspoon
(74) *Attorney, Agent, or Firm*—Lorusso, Loud & Kelly

(57) ABSTRACT

A lactam-aldehyde compound represented by the formula (I) shown in the specification. The lactam-aldehyde compound may be prepared by subjecting a lactone-imine compound represented by formula (III) shown in the specification to an isomerization reaction. The precursor lactone-imine compound may be prepared by rearrangement of a 3,5-dioxa-12-azawurtzitane compound.

7 Claims, No Drawings

LACTAM-ALDEHYDE COMPOUND AND PROCESS OF PREPARING SAME

BACKGROUND OF THE INVENTION

This invention relates to a lactam-aldehyde compound and a process of preparing same. The present invention is also directed to a lactone-imine compound useful as a precursor of the lactam-aldehyde compound and a process of preparing same.

The present inventors have proposed a 3,5-dioxa-12-azawurtzitane compound represented by the following formula (IV):

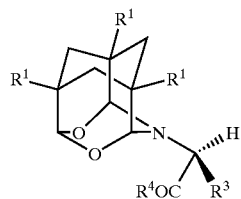

(IV)

wherein $R^1$ represents an alkyl group, $R^3$ represents a group which, together with a —$CH(NH_2)COOH$ group, constitutes an α-amino acid of the formula $R^3CH(NH_2)COOH$ and which may contain one or more substituents and $R^4$ represents a hydroxyl group or a group obtained by removing a hydrogen atom of the terminal amino group of an oligo- or polypeptide or a polyamino acid (EP-A-1153926 and U.S. patent application Ser. No. 09/733,063).

The 3,5-dioxa-12-azawurtzitane compound does not have any site into which other functional groups may be introduced.

SUMMARY OF THE INVENTION

It is an object of the present invention to provide a lactam-aldehyde compound having a lactam site and a formyl group into which other functional groups may be introduced.

Another object of the present invention is to provide a compound of the above-mentioned type which has a structure similar to an amino acid or a polypeptide.

It is a further object of the present invention to provide a process for the production of the above lactam-aldehyde compound.

It is yet a further object of the present invention to provide a lactone-imine compound which is useful as a precursor of the above lactam-aldehyde compound.

In accordance with one aspect of the present invention, there is provided a lactam-aldehyde compound represented by the following formula (I):

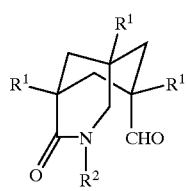

(I)

wherein $R^1$ represents an alkyl group, $R^2$ represents an organic group.

In another aspect, the present invention provides a lactam-aldehyde compound as claimed in claim 1, and represented by the following formula (II)

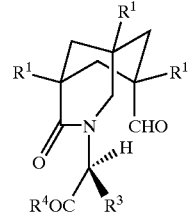

(II)

wherein $R^1$ is as defined above, $R^3$ is an amino acid side chain group and $R^4$ is a hydroxyl group or a peptide chain.

The present invention also provides a lactone-imine compound represented by the following formula (III):

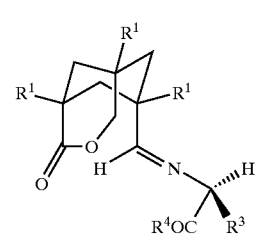

(III)

wherein $R^1$ is as defined above, $R^3$ is an amino acid side chain group and $R^4$ is a hydroxyl group or a peptide chain.

The present invention further provides a process for the production of a lactam-aldehyde compound of the following formula (II):

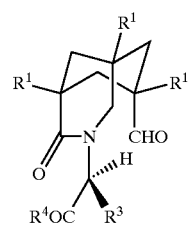

(II)

wherein $R^1$ represents an alkyl group, $R^3$ is an amino acid side chain group and $R^4$ is a hydroxyl group or a peptide chain, said process comprising subjecting a lactone-imine compound to an isomerization reaction, said lactone-imine compound being represented by the following formula (III):

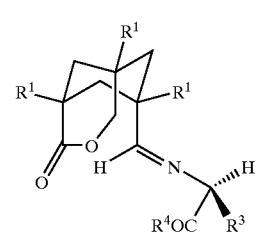

(III)

wherein $R^1$, $R^3$ and $R^4$ are as defined above.

The present invention further provides a process for the production of a lactone-imine compound of the following formula (III):

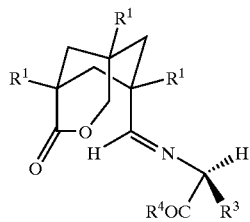

(III)

wherein R¹ represents an alkyl group, R³ is an amino acid side chain group and R⁴ is a hydroxyl group or a peptide chain, said process comprising subjecting a 3,5-dioxa-12-azawurtzitane compound to molecular rearrangement, said 3,5-dioxa-12-azawurtzitane compound being represented by the following formula (IV):

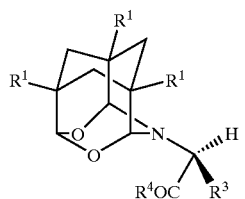

(IV)

wherein R¹ represents an alkyl group, R³ is an amino acid side chain group and R⁴ is a hydroxyl group or a peptide chain.

In the present specification and claims, the three R¹s bonded to the carbon atoms of the lactam-aldehyde compound of the formula (I) or (II) may be the same or different alkyl groups.

The new class of lactam-aldehyde compounds of the present invention have a lactam site and a formyl group into which other functional groups may be introduced and are able to possess a structure similar to an amino acid or a polypeptide. Therefore, the compounds of the present invention will be utilizable for various applications, for example, as a molecular recognition agent for use in neurotransmission studies, an intermediate for a protein-resembling compound, a surfactant, a protective group and a host-guest complex for use as a sensor.

Other objects, features and advantages of the present invention will be apparent from the detailed description of the preferred embodiments of the invention to follow.

DETAILED DESCRIPTION OF THE PREFERRED EMBODIMENTS OF THE INVENTION

A lactam-aldehyde compound of the present invention is represented by the above formula (I). In the formula (I), $R^1$ represents an alkyl group preferably having 1–12 carbon atoms. Illustrative of suitable alkyl groups of $R^1$ are methyl, ethyl, propyl, butyl, pentyl, hexyl, heptyl, octyl, nonyl, decyl and structural isomers thereof.

The symbol $R^2$ represents an organic group. The organic group is preferably a group represented by the formula —Z—Y in which Z represents a direct bond or an alkylene group and Y represents a group having an active hydrogen. Specific examples of the organic group include carboxyl, carboxyalkyl, amino, aminoalkyl, imidazolyl, imidazolylalkyl, indolyl, indolylalkyl, hydroxyphenyl, hydroxyphenylalkyl, pyridyl, pyridylalkyl, aminophenyl, aminophenylalkyl, hydroxyl, hydroxyalkyl, glycoloyl, glycoloylalkyl, glyceroyl, glyceroylalkyl, mercapto, mercaptoalkyl, carboxyaminoethylenedithio and carboxyaminoethylenedithioalkyl.

Another class of preferred organic group $R^2$ is represented by —$CHR^3COR^4$ where $R^3$ is an amino acid side chain group and $R^4$ is a hydroxyl group or a peptide chain.

The term "amino acid side chain group" as used herein refers to the amino acid functional "R" side chains of any amino acid-based compound, including but not limited to any of the known twenty two amino acids, including alanine, arginine, asparagine, aspartic acid, cysteine, cystine, glutamic acid, glutamine, glycine, histidine, hydroxyproline, isoleucine, leucine, lysine, methionine, phenylalanine, proline, serine, threonine, tryptophan, tyrosine and valine, i.e., the substituents on the amino acid carbon atom located between the amino group and carboxylic acid functionalities of the amino acids such as described above. The amino acid side chain group may contain one or more substituents such as an alkyl group, an acetyl group, an alkoxy group, a benzoxycarbonyl group, a tert-butoxycarbonyl group, a 9-fluorenylmethoxycarbonyl group and a 1,7,9-trialkyl-3,5-dioxa-12H-azawurtzitan-12-yl group.

The peptide chain $R^4$ may be an oligopeptide (composed of 2 to 9 amino acids), a polypeptide (composed of 10 or more amino acids, generally 10–100 amino acids) or a polyamino acid (composed of two or more same amino acids) and is linked through a terminal amino group thereof to the carbonyl group of —$CHR^3COR^4$. The amino acids constituting the peptide chain $R^4$ may be, for example, those as described previously.

Some examples of lactam-aldehyde compounds of the present invention are shown in Table 1 in which $R^1$, $R^3$ and $R^4$ are the symbols of the formula (II). The lactam-aldehyde compounds of the present invention, however, are of course not limited to those specifically exemplified compounds. For example, the groups $R^1$, $R^3$ and $R^4$ listed in Table 1 may be arbitrarily selected for any desired combination.

TABLE 1

| $R^1$ | $R^3$ | $R^4$ |
|---|---|---|
| $CH_3$ | H | $(His)_n$ |
| $CH_3$ | $CH_3$ | $(Gly)_n$ |
| $CH_3CH_2$ | $(CH_3)_2CH$ | $(Ala)_n$ |
| $CH_3CH_2CH_2$ | $(CH_3)_2CHCH_2$ | $(Val)_n$ |
| $CH_3(CH_2)_3$ | $CH_3CH_2(CH_3)CH$ | $(Leu)_n$ |
| $CH_3(CH_2)_4$ | ⟨benzyl: C₆H₅–CH₂⟩ | $(Phe)_n$ |
| $CH_3(CH_2)_5$ | ⟨4-hydroxybenzyl: HO–C₆H₄–CH₂⟩ | $(Tyr)_n$ |
| H | ⟨indol-3-ylmethyl⟩ | $(Try)_n$ |
| $(CH_3)_2CH$ | $HOCH_2$ | $(Ser)_n$ |
| $(CH_3)_3C$ | $CH_3(OH)CH$ | $(Thre)_n$ |
| $(CH_3)_2CHCH_2$ | $HSCH_2$ | $(CySH)_n$ |

TABLE 1-continued

| R¹ | R³ | R⁴ |
|---|---|---|
| $(CH_3)_2CH(CH_2)_2$ | HOOC(NH$_2$)CH\|CH$_2$SSCH$_2$ | $(CyS-SCy)_n$ |
| $(CH_3)_3C(CH_2)_3$ | $CH_3SCH_2CH_2$ | $(Meth)_n$ |
| $CH_3CH_2CH_2$ | $HOOCCH_2$ | $(Asp)_n$ |
| $CH_3(CH_2)_9$ | $HOOCCH_2CH_2$ | $(Glu)_n$ |
| $CH_3$ | $H_2NCH_2(CH_2)_3$ | $(Lys)_n$ |
| $CH_3$ | $HN=C(NH_2)NH(CH_2)_3$ | $(Arg)_n$ |
| $CH_3$ | 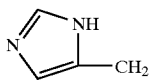 | OH |

In Table 1, n is an integer.

The lactam-aldehyde compounds of the formula (II) may be prepared by subjecting a lactone-imine compound of the above formula (III) to isomerization.

The isomerization may be carried out by dissolving the lactone-imine compound in an aqueous solvent or a hydrophilic polar organic solvent to obtain a solution. The solution is then allowed to stand at a temperature and for a period sufficient to obtain the lactam-aldehyde compound. The reaction temperature is not specifically limited but is generally in the range of 0–70° C. The reaction time is generally 10 hours to 1 month.

The hydrophilic polar organic solvent may be, for example, an aprotic solvent such as acetonitrile, acetone, dimethylsulfoxide or dimethylformamide. The aqueous solvent may be, for example, water, an aqueous buffer solution or a mixed solvent containing water and a hydrophilic polar organic solvent.

After the isomerization reaction, the solvent is removed by any known method preferably by distillation under a reduced pressure or by lyophilization. The crude product thus obtained may be purified by any conventional method such as chromatography.

The lactone-imine compound of the above formula (III) may be produced by hydride rearrangement of a 3,5-dioxa-12-azawurtzitane compound represented by the above formula (IV). The preparation of the 3,5-dioxa-12-azawurtzitane compound is disclosed in EP-A-1153926 and U.S. patent application Ser. No. 09/733,063, the disclosure of which is hereby incorporated by reference herein.

The rearrangement reaction of the 3,5-dioxa-12-azawurtzitane compound may be carried out by dissolving the 3,5-dioxa-12-azawurtzitane compound in an aqueous solvent or a hydrophilic polar organic solvent to obtain a solution. The solution is then allowed to stand at a temperature and for a period sufficient to obtain the lactone-imine compound. The reaction temperature is not specifically limited but is generally in the range of 0–70° C. The reaction time is generally 10 hours to 10 days.

The hydrophilic polar organic solvent may be, for example, an aprotic solvent such as acetonitrile, acetone, dimethylsulfoxide or dimethylformamide. The aqueous solvent may be, for example, water, an aqueous buffer solution or a mixed solvent containing water and a hydrophilic polar organic solvent. After the rearrangement reaction, the solvent is removed by any known method preferably by distillation under a reduced pressure or by lyophilization. The crude product thus obtained may be purified by any conventional method such as recrystallization and/or chromatography.

The following examples will further illustrate the present invention.

EXAMPLE 1

Preparation of Lactone-Imine Compound:

3,5-Dioxa-12-azawurtzitane compound (50 mg) of the formula (IV) in which $R^1$ is a methyl group, $R^3$ is a hydrogen atom and $R^4$ is —OK was dissolved in a mixed solvent composed of water and acetonitrile and the solution was stirred for 3 days at room temperature. The solvent was then removed from the reaction mixture under a reduced pressure to obtain a crude product. This was purified by an ion-exchange chromatography to obtain 38 mg (yield: 87%) of a lactone-imine compound of the formula (III) in which $R^1$ is a methyl group, $R^3$ is a hydrogen atom and $R^4$ is a hydroxyl group. The results of the NMR analysis of the product are shown below.

$^1$H NMR (acetonitrile-d$_3$/D$_2$O): δ 0.99 (s, 3H, methyl H), 1.07 (s, 3H, methyl H), 1.11 (d, 1H, J=14.0 Hz, methylene H), 1.29 (s, 3H, methyl H), 1.34 (d, 2H, J=13.7 Hz, methylene H), 1.59 (d, 1H, J=12.9 Hz, methylene H), 2.34 (d, 1H, J=14.0 Hz, methylene H), 2.51 (d, 1H, J=13.9 Hz, methylene H), 3.54 (s, 2H, methylene H), 4.01 (d, 1H, J=15.9 Hz, methylene H), 4.34 (d, 1H, J=15.9 Hz, methylene H), 8.23 (s, 1H, imine H).

Preparation of Lactam-Aldehyde Compound:

Lactone-imine compound (25 mg) of the formula (III) in which $R^1$ is a methyl group, $R^3$ is a hydrogen atom and $R^4$ is —OK was dissolved in dimethylsulfoxide and the solution was stirred for 5 days at room temperature. The solvent was then removed from the reaction mixture with heating under a reduced pressure to obtain a crude product. This was purified by an ion-exchange chromatography to obtain 20 mg (yield: 91%) of a lactam-aldehyde compound of the formula (II) in which $R^1$ is a methyl group, $R^3$ is a hydrogen atom and $R^4$ is a hydroxyl group. The results of the NMR analysis of the product are shown below.

$^1$H NMR (acetonitrile-d$_3$/D$_2$O): δ 0.82 (s, 3H, methyl H), 0.91 (s, 3H, methyl H), 1.06 (s, 3H, methyl H), 1.15 (d, 1H, J=14.1 Hz, methylene H), 1.25 (dd, 1H, J=12.8 Hz, J=1.8 Hz, methylene H), 1.25 (d, 1H, J=14.2 Hz, methylene H), 1.80 (d, 1H, J=12.8 Hz, methylene H), 2.15 (d, 1H, J=14.1 Hz, methylene H), 2.21 (d, 1H, J=14.2 Hz, methylene H), 2.71 (dd, 1H, J=12.4 Hz, J=1.8 Hz, methylene H), 2.81 (d, 1H, J=16.9 Hz, methylene H), 3.26 (d, 1H, J=12.4 Hz, methylene H), 4.13 (d, 1H, J=16.9 Hz, methylene H), 9.09 (s, 1H, formyl H).

EXAMPLE 2

Preparation of Lactone-Imine Compound:

3,5-Dioxa-12-azawurtzitane compound (128 mg) of the formula (IV) in which $R^1$ is a methyl group, $R^3$ is a hydrogen atom and $R^4$ is —ONa was dissolved in a mixed solvent composed of water and acetonitrile and the solution was stirred for 5 days at room temperature. The solvent was then removed from the reaction mixture under reduced pressure to obtain a crude product. This was recrystallized to obtain 109 mg (yield: 85%) of a lactone-imine compound of the formula (III) in which $R^1$ is a methyl group, $R^3$ is a hydrogen atom and $R^4$ is —ONa. The results of the NMR analysis of the product are shown below. $^1$H NMR (acetonitrile-d$_3$/D$_2$O): δ 0.97 (s, 3H, methyl H), 0.98 (s, 3H, methyl H), 1.05 (d, 1H, J=14.1 Hz, methylene H), 1.23 (d, 1H, J=13.7 Hz, methylene H), 1.26 (s, 3H, methyl H), 1.30 (d, 1H, J=12.8 Hz, methylene H), 1.55 (d, 1H, J=12.8 Hz, methylene H), 2.34 (d, 1H, J=14.1 Hz, methylene H), 2.51 (d, 1H, J=13.7 Hz, methylene H), 3.47 (d, 1H, J=15.9 Hz, methylene H), 3.58 (d, 1H, J=15.9 Hz, methylene H), 4.02 (d, 1H, J=16.2

Hz, methylene H), 4.35 (d, 1H, J=16.2 Hz, methylene H), 8.15 (s, 1H, imine H). The results of MS(ESI): m/z 266 (M−Na)

Preparation of Lactam-Aldehyde Compound:

The lactone-imine compound obtained above (10 mg) was dissolved in dimethylsulfoxide and the solution was stirred for 7 days at room temperature. The solvent was then removed from the reaction mixture under reduced pressure to obtain a crude product. This was purified by chromatography to obtain 6 mg (yield: 60%) of a lactam-aldehyde compound of the formula (II) in which $R^1$ is a methyl group, $R^3$ is a hydrogen atom and $R^4$ is —ONa. The results of the NMR analysis of the product are shown below. $^1$H NMR (DMSO-d$_6$): δ 0.79 (s, 3H, methyl H), 0.88 (s, 3H, methyl H), 1.03 (s, 3H, methyl H), 1.09 (dt, 1H, J=13.6 Hz, J=1.7 Hz, J=1.0 Hz, methylene H), 1.20 (d, 1H, J=13.7 Hz, methylene H), 1.27 (dd, 1H, J=12.5 Hz, J=2.1 Hz, methylene H), 1.64 (d, 1H, J=12.5 Hz, methylene H), 2.10 (d, 1H, J=13.6 Hz, methylene H), 2.16 (d, 1H, J=13.7 Hz, methylene H), 2.27 (d, 1H, J=15.9 Hz, methylene H), 2.46 (dd, 1H, J=11.8 Hz, J=2.1 Hz, methylene H), 3.40 (dd, 1H, J=11.8 Hz, J=1.7 Hz, methylene H), 4.05 (d, 1H, J=15.9 Hz, methylene H), 9.00 (d, 1H, J=1.0 Hz, formyl H).

EXAMPLE 3

Preparation of Lactone-Imine Compound:

3,5-Dioxa-12-azawurtzitane compound (58 mg) of the formula (IV) in which $R^1$ is a methyl group, $R^3$ is a hydrogen atom and $R^4$ is —Gly (carboxyl group of Gly is in the form of —COOK) was dissolved in a mixed solvent composed of water and acetonitrile and the solution was stirred for 7 days at 50° C. The solvent was then removed from the reaction mixture under reduced pressure to obtain a crude product. This was recrystallized to obtain 35 mg (yield: 60%) of a lactone-imine compound of the formula (III) in which $R^1$ is a methyl group, $R^3$ is a hydrogen atom and $R^4$ is —Gly (carboxyl group of Gly is in the form of —COOK). The results of the NMR analysis of the product are shown below. $^1$H NMR (acetonitrile-d$_3$/D$_2$O): δ 8.31 (s, 1H, imine H)

Preparation of Lactam-Aldehyde Compound:

The lactone-imine compound obtained above (35 mg) was dissolved in a mixed solvent composed of water and acetonitrile and the solution was stirred for 3 weeks at 50° C. The solvent was then removed from the reaction mixture under reduced pressure to obtain a crude product. This was purified by chromatography to obtain 8 mg (yield: 23%) of a lactam-aldehyde compound of the formula (II) in which $R^1$ is a methyl group, $R^3$ is a hydrogen atom and $R^4$ is —Gly (carboxyl group of Gly is in the form of —COOK). The results of the NMR analysis of the product are shown below. $^1$H NMR (acetonitrile-d$_3$/D$_2$O): δ 9.11 (s, 1H, formyl H)

EXAMPLE 4

3,5-Dioxa-12-azawurtzitane compound (50 mg) of the formula (IV) in which $R^1$ is a methyl group, $R^3$ is a hydrogen atom and $R^4$ is —His—Lys (carboxyl terminal of Lys is in the form of —COONa) was dissolved in a mixed solvent composed of water and acetonitrile and the solution was stirred for 5 days at room temperature. The solvent was then removed from the reaction mixture under reduced pressure to obtain a crude product. This was recrystallized to obtain 35 mg (yield: 70%) of a lactone-imine compound of the formula (III) in which $R^1$ is a methyl group, $R^3$ is a hydrogen atom and $R^4$ is —His—Lys (carboxyl terminal of Lys is in the form of —COONa). The results of the NMR analysis of the product are shown below. $^1$H NMR (acetonitrile-d$_3$/D$_2$O): δ 8.18 (s, 1H, imine H), 8.20 (s, 1H, imine H).

The results of MS(ESI): m/z 723 (M−Na).

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A lactam-aldehyde compound represented by the following formula (I):

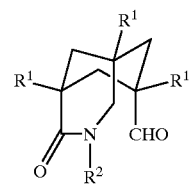

(I)

wherein $R^1$ represents an alkyl group, $R^2$ represents an organic group.

2. A lactam-aldehyde compound as claimed in claim 1, and represented by the following formula (II)

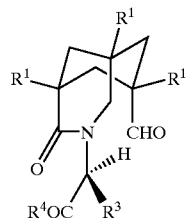

(II)

wherein $R^1$ is as defined above, $R^3$ is an amino acid side chain group and $R^4$ is a hydroxyl group or a peptide chain.

3. A lactam-aldehyde compound as claimed in claim 1, wherein the organic group is represented by the formula —Z—Y in which Z represents a direct bond or an alkylene group and Y represents a group having an active hydrogen.

4. A lactam-aldehyde compound as claimed in claim 1, wherein the organic group is selected from carboxyl, carboxyalkyl, amino, aminoalkyl, imidazolyl, imidazolylalkyl, indolyl, indolylalkyl, hydroxyphenyl, hydroxyphenylalkyl, pyridyl, pyridylalkyl, aminophenyl, aminophenylalkyl, hydroxyl, hydroxyalkyl, glycoloyl, glycoloylalkyl, glyceroyl, glyceroylalkyl, mercapto, mercaptoalkyl, carboxyaminoethylenedithio and carboxyaminoethylenedithioalkyl.

5. A lactone-imine compound represented by the following formula (III):

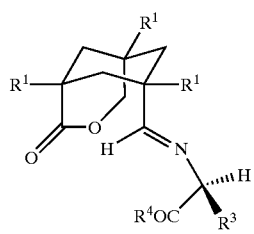

wherein $R^1$ is as defined above, $R^3$ is an amino acid side chain group and $R^4$ is a hydroxyl group or a peptide chain.

6. A process for the production of a lactam-aldehyde compound of the following formula (II):

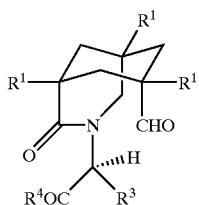

wherein $R^1$ represents an alkyl group, $R^3$ is an amino acid side chain group and $R^4$ is a hydroxyl group or a peptide chain, said process comprising subjecting a lactone-imine compound to an isomerization reaction, said lactone-imine compound being represented by the following formula (III):

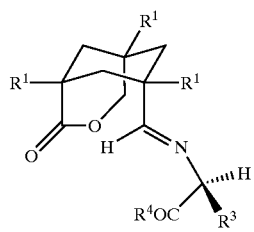

wherein $R^1$, $R^3$ and $R^4$ are as defined above.

7. A process for the production of a lactone-imine compound of the following formula (III):

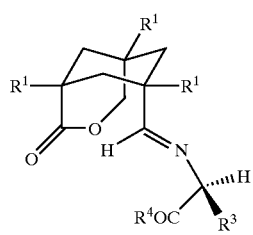

wherein $R^1$ represents an alkyl group, $R^3$ is an amino acid side chain group and $R^4$ is a hydroxyl group or a peptide chain, said process comprising subjecting a 3,5-dioxa-12-azawurtzitane compound to molecular rearrangement, said 3,5-dioxa-12-azawurtzitane compound being represented by the following formula (IV):

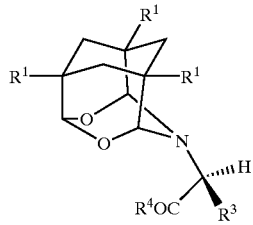

wherein $R^1$ represents an alkyl group, $R^3$ is an amino acid side chain group and $R^4$ is a hydroxyl group or a peptide chain.

* * * * *